ja et al.

(12) United States Patent
Khanuja et al.

(10) Patent No.: US 7,291,349 B2
(45) Date of Patent: Nov. 6, 2007

(54) ANTI-DERMATOPHYTIC PREPARATION AND USE THEREOF

(76) Inventors: Suman Preet Singh Khanuja, c/o Central Institute of Medicinal and Aromtic Plants, P.O. CIMAP., Lucknow, Uttar Pradesh (IN); Pushplata Chaturvedi, c/o Central Institute of Medicinal and Aromatic Plants, P.O. CIMAP., Lucknow, Uttar Pradesh (IN); Anil Kumar Singh, c/o Central Institute of Medicinal and Aromatic Plants P.O. CIMAP., Lucknow, Uttar Pradesh (IN); Ajit Kumar Shasany, c/o Central Institute of Medicinal and Aromatic Plants, P.O. CIMAP., Lucknow, Uttar Pradesh (IN); Vinay Kumar Agarwal, c/o Central Institute of Medicinal and Aromatic Plants, P.O. CIMAP., Lucknow, Uttar Pradesh (IN); Vivek Kumar Gupta, c/o Central Institute of Medicinal and Aromatic Plants, P.O. CIMAP., Lucknow, Uttar Pradesh (IN); Subhash Chandra Gupta, c/o Central Instutite of Medicinal and Aromatic Plants, P.O. CIMAP., Lucknow, Uttar Pradesh (IN); Arun Kumar Tripathy, c/o Central Instutite of Medicinal and Aromatic Plants, P.O. CIMAP., Lucknow, Uttar Pradesh (IN); Anirban Pal, c/o Central Instutite of Medicinal and Aromatic Plants, P.O. CIMAP., Lucknow, Uttar Pradesh (IN); Dharmendra Saikia, c/o Central Institute of Medicinal and Aromatic Plants, P.O. CIMAP., Lucknow, Uttar Predesh (IN); Mahendra Pandurang Darokar, c/o Central Institute of Medicinal and Aromatic Plants, P.O. CIMAP., Lucknow, Uttar Pradesh (IN); Krishna Kumar Aggarwal, c/o Central Institute of Medicinal and Aromatic Plants, P.O. CIMAP., Lucknow, Uttar Pradesh (IN); Ravi Prakash Bansal, C/o Central Institute of medicinal and Aromatic Plants P.O. CIMAP., Lucknow, Uttar Pradesh (IN)

( * ) Notice: Subject to any disclaimer, the term of this patent is extended or adjusted under 35 U.S.C. 154(b) by 178 days.

(21) Appl. No.: 10/761,804

(22) Filed: Jan. 21, 2004

(65) Prior Publication Data
US 2005/0181081 A1  Aug. 18, 2005

Related U.S. Application Data

(63) Continuation of application No. 10/435,617, filed on May 9, 2003, now abandoned.

(51) Int. Cl.
*A01N 65/00* (2006.01)
(52) U.S. Cl. ...................................... 424/725
(58) Field of Classification Search .................... None
See application file for complete search history.

(56) References Cited

U.S. PATENT DOCUMENTS

| 6,197,305 | B1 * | 3/2001 | Friedman et al. | 424/737 |
| 6,277,374 | B1 * | 8/2001 | Vandenbergh et al. | 424/115 |
| 6,429,231 | B1 * | 8/2002 | Bhagwat et al. | 514/603 |
| 2002/0068142 | A1 * | 6/2002 | Baroni et al. | 428/43 |

* cited by examiner

*Primary Examiner*—Patricia Leith
*Assistant Examiner*—Qiuwen Mi
(74) *Attorney, Agent, or Firm*—Ladas & Parry LLP

(57) ABSTRACT

The present invention provides an improved preparation based on the synergistic action of garlic extract and essential oil of *M. spicata* var. Ganga or cinnamon oil against dermatophytic fungus. More particularly, the present invention relates to the synergistic enhancement of activity of a combination by menthyl acetate or Geraniol. The invention also provides a method of preparation of the synergistic combination and the shelf life observed to be more than one year. The cream based preparation is a potent anti-dermatophytic as described and illustrated by in vitro and in vivo evaluations.

26 Claims, No Drawings

US 7,291,349 B2

ANTI-DERMATOPHYTIC PREPARATION AND USE THEREOF

This application is a continuation of application Ser. No. 10/435,617 filed on May 9, 2003 now abandoned.

FIELD OF INVENTION

The present invention provides an improved preparation based on the synergistic action of garlic extract and essential oil of *M. spicata* var. Ganga or cinnamon oil against dermatophytic fungus. More particularly, the present invention relates to the synergistic enhancement of activity of a combination by menthyl acetate or Geraniol. The invention also provides a method of preparation of the synergistic combination and the shelf life observed to be more than one year. The cream based preparation is a potent anti-dermatophytic as described and illustrated by in vitro and in vivo evaluations.

BACKGROUND OF THE INVENTION

Garlic, *Allium sativum* L (*Liliaceae*) has been used traditionally to treat a number of infectious diseases including those caused by bacteria, fungi, protozoa and viruses (Nor best. D. Weber et al. 1992, Planta Medica 58:418). Beside these, it has also been used for broad range of therapeutic properties including anti-inflammatory, anti-diabetic, anti-atherogenic, anti-coagulant anti-cancer and neurotropic. (M. Colic. et al Phytomedicine 9:117-124. 2002).

A number of reports are available on in vitro and in vivo efficacy of garlic oil, juice, extract (water or solvent) or lyophilised water extract against plant and human pathogens causing fungal and bacterial infections. The activity of garlic against dermatophytosis i.e. the superficial infections of skin or keratinised tissue of man and animals can be very well visualised from the reports of Venugopal and Venugopal 1995 and Prasad et al 1982, 1983 and 1987. Venugopal, 1995 [International Journal of Dermatology 34(4) 278-279] reported the activity of garlic extracts against 88 clinical isolates of dermatophytes by agar dilution technique, which includes *Microsporum cannis, M, audouinii Trichophyton rubrum T mentagraphytes, T violaccum, T simii, T verrucosum T erinacci* and *Epidermophytn floccosum*. while Prasad et al, 1982, 1983 reported clinical findings of garlic extract against dermatophytes in animals and human beings, [Indian Journal of Medical research 1982 465-467, Indian Veterinary Medical journal 1983 7 (3) 161-163 and Poultry science 1981 60 (3) 541-545 Indian Veterinary Medical journal 1987 11 (2) 108-110] Besides these reports, many workers have described effect of garlic extract against isolated or experimental infections, those include the work of Sharma S. R. et al 1994 [International journal of Animal sciences 9 (2) 239-240.] Sharma M. C. [Indian Veterinary Journal 1990 67 (3) 269-271,] Thakur D K et al [Indian journal of Animal-Health 1987 26 (1) 31-34 & Indian veterinary journal 1983 60 (10) 799-801] Upadhyay. M P et al 1980 [Journal of general & applied microbiology 1980 26 6, 421-424.] Rajora V. S. Indian Veterinary Journal 1982. 59 (10) 815-817.

All the above reports and many others have utilized garlic extract (solvent or water), juice, or oil for the in vitro or in vivo evaluation of the infections caused by various species of dermatophytes viz. *Trichophyton Microsporum Epidermophyton* and yeast like fungi of genera *Canddia, Ccryptococcus,Rhodotorula. Torulopsis trichosporon*. It is also evident from the above reports that Garlic can be utilized in broad spectrum antifungal preparation for topical application but the instability of the activity and the disagreeable smell are two main constraints in its formulations as the activity of garlic juice/extract degrade & finally lost on storage and higher concentration produces disagreeable smell. The loss in activity due to storage may be attributed to the fact that garlic possesses unstable compounds. Up to now more than 200 different biologically active substances has been isolated from garlic, among them organosulphur compounds such as allicin azoenes, diallyltrisulfide (DATS) or s-allylcystein, are considered the most important biologically active compound found in crushed or homogenised garlic [Colic M et. al. Phytomedicine 2000 9 117-124]. It is unstable in the presence of heat or organic solvent and forms a variety of degraded compounds. Allicin is not present in garlic but is rapidly procured when its precursor alliin is cleaved by alliinase upon crushing or mincing of garlic because allin and alliinase are very stable when dry. Garlic powders have potential to preserve allin without degradation the allicin. However some powder preparations do release allicin upon aqueous contact which vary depending upon the source.

Due to pronounced antibacterial and antifungal properties garlic have been used as insecticides to control plant diseases such as army worms, aphids and Colorado beetles. Anderson et al, U.S. Pat. No. 5,733,552 has utilised garlic extract & water to repel mosquito.

Hsu, et al, 2001, U.S. Pat. No. 6,231,685 entitle "Natural pesticide" has utilized garlic oil or extracts in combination with essential oils and found an improvement in insecticidal and fungicidal activity. They have utilized various combinations to control insects and fungal infection on plants. The invention also describes a synergistic effect of garlic oil or extract combined with essential oils, resulting in improved insecticidal, fungicidal activities. The essential oils described in this patent are cotton seed oil, soyabean oil, cinnamon oil corn oil, cedar oil, castor oil, clove oil, geranium oil, lemon grass oil, linseed oil, mint oil, sesame oil, thyme oil, rosemary oil, anise oil, basil oil, camphor oil, citronella oil, Eucalyptus oil, Fennel oil, Ginger oil, grapefruit oil, lemon oil, mandarin oil, orange oil, pine needle oil, pepper oil, rose oil, tangerine oil, tea tree oil, tee seed oil, mineral and fish oil.

But till today no report is available on synergism of the garlic extract with plant essential oils or constituents for stable anti-dermatophytic activity. The invention is novel as the formulation uses the essential oil of the plant *Mentha spicata* var Ganga. This improved formulation from plant source is highly potent in in vitro and in vivo evaluations. This improved preparation against dermatophytic fungus is novel due to better synergism in activity, better stability and shelf life and reduced smell of garlic which is masked by the other ingredients.

OBJECTS OF THE INVENTION

The main object of the present invention is to develop a herbal formulations active against broad spectrum of dermatophytic fungi.

Another object of the invention is to provide a formulation useful as a topical cream, which smoothens the skin and allows slow absorption of the contents, there by causing effective action, which completely eliminates the infection caused by dermatophytic fungi.

Yet another object of the invention is to provide an antifungal formulation containing garlic extract (*Allium sati-*

*vum*) where the smell of garlic is masked and the product bears pleasant and agreeable smell.

Yet another object of the invention is to provide an antifungal formulation having combination of garlic extract, essential oil and certain constituents of essential oil to amplify the synergistic effects.

Yet another object of the invention is to provide an antifungal formulation which is commercially viable and cheaper as compared to other creams available in the market.

Yet another object of the invention is to provide an anti-dermatophytic formulation which is totally natural and has not any preservative.

Yet another object of the invention is to provide a garlic based anti-dermatophytic cream which has long shelf life period.

SUMMARY OF THE INVENTION

The invention provides a novel formulation based on the synergistic action of garlic extract and essential oil of *M. spicata* var Ganga or cinnamon oil alone or in combination with both which may further be enhanced by menthyl acetate or Geraniol. Further the invention provides a method of preparation of the synergistic combination. The shelf life of the said invention was observed to be more than one year. The oil of *M. spicata* var Ganga act as preservative for the cream. The cream is a potent anti-dermatophytic as described and illustrated and evaluated in human volunteers.

Accordingly, the present invention provides a novel synergistic antifungal formulation active against dermatophytic fungi comprising a garlic extract in propylene glycol, essential oil of *M. spicata* Var Ganga or cinnamon oil alone or in combination along with menthyl acetate or geraniol in suitable base.

In one embodiment of the invention, the base is prepared by mixing stearyl alcohol, cetyl alcohol and propylene glycol at 70-75° C. over water bath and cooling down the preparation with constant stirring up to ambient temperature and finally curing for 48 hours in covered beaker with occasional mixing the product.

In another embodiment of the invention, the garlic extract is present in an amount of 1-3% and the essential oil of *Mentha spicata* var Ganga or cinnamon oil alone or in combination is present in an amount of 2%-5% and wherein constituents of essential oil like menthyl acetate or geraniol is added to the base at temperature 30-35° C.

In another embodiment of the invention, the garlic extract in propylene glycol is present in a concentration in the range of 1%-2.5%.

In yet another embodiment of the invention, the essential oil of *M. spicata* var Ganga is present in a concentration in the range of 2%-5%.

In a further embodiment of the invention, the cinnamon essential oil is present in a concentration in the range of 0.01%-0.8%

In yet another embodiment of the invention, the menthyl acetate is present in a concentration in the range of 0.3%-1.2%

In a further embodiment of the invention, the concentration of geraniol is about 1%.

In yet another embodiment of the invention, the dermatophytic fungi are selected from the group consisting of *Candida, Trichophyton, Microsporum* and *Epidermophyton.*

In another embodiment of the invention, the shelf life of the formulation is more than one year.

The synergistic/enhancing activity of garlic extract on essential oils as the minimum inhibitory concentrations of the essential oils were decreased to several folds in presence of the garlic extract (Propylene glycol) indicating the enhancing and synergistic activity of garlic extract on activity of essential oils.

In yet another embodiment of the invention, the synergistic antifungal preparation of the invention active against dermatophytic fungi comprises of garlic extract in propylene glycol, essential oil of *M. spicata* Var Ganga or cinnamon oil alone or in combination, along with menthyl acetate or geraniol in suitable base wherein the improved formulation act by inhibiting the ergosterol biosynthesis.

In yet another embodiment of the invention, the formulation is active against dermatophytic fungi by making the sterol non-available for cell membrane biosynthesis.

In a further embodiment of the invention, the antifungal formulation is active against dermatophytic fungi, wherein the fungi may or may not be sensitive to synthetic antifungal compounds selected from the group consisting of azoles and polyenes.

In another embodiment of the invention, the antifungal formulation is active against dermatophytic fungi and the antifungal formulation shows clearing of the fungal culture indicating clear lysis.

The present invention also relates to a method for the treatment of dermatophytic fungi comprising administering to a subject infected with the dermatophytic fungi an effective amount of a antifungal preparation comprising a garlic extract in propylene glycol, essential oil of *M. spicata* Var Ganga or cinnamon oil alone or in combination along with menthyl acetate or geraniol in suitable base.

In one embodiment of the invention, the base is prepared by mixing stearyl alcohol, cetyl alcohol and propylene glycol at 70-75° C. over water bath and cooling down the preparation with constant stirring up to ambient temperature and finally curing for 48 hours in covered beaker with occasional mixing the product.

In another embodiment of the invention, the garlic extract is present in an amount of 1-3% and the essential oil of *Mentha spicata* var Ganga or cinnamon oil alone or in combination is present in an amount of 2%-5% and wherein constituents of essential oil like menthyl acetate or geraniol is added to the base at temperature 30-35° C.

In another embodiment of the invention, the garlic extract in propylene glycol is present in a concentration in the range of 1%-2.5%.

In yet another embodiment of the invention, the essential oil of *M. spicata* var Ganga is present in a concentration in the range of 2%-5%.

In a further embodiment of the invention, the cinnamon essential oil is present in a concentration in the range of 0.01%-0.8%

In yet another embodiment of the invention, the menthyl acetate is present in a concentration in the range of 0.3%-1.2%

In a further embodiment of the invention, the concentration of geraniol is about 1%.

In yet another embodiment of the invention, the dermatophytic fungi are selected from the group consisting of *Candida, Trichophyton, Microsporum* and *Epidermophyton.*

In another embodiment of the invention, the shelf life of the formulation is more than one year.

In yet another embodiment of the invention, the formulation is active against dermatophytic fungi by making the sterol non-available for cell membrane biosynthesis.

In a further embodiment of the invention, the antifungal formulation is active against dermatophytic fungi wherein the fungi may or may not be sensitive to synthetic antifungal compounds selected from the group consisting of azoles and polyenes.

In another embodiment of the invention, the antifungal formulation is active against dermatophytic fungi and the antifungal formulation shows clearing of the fungal culture indicating clear lysis.

DETAILED DESCRIPTION

The improved formulation was carefully planned, experimented and evaluated in vitro and in vivo as described and illustrated below.

EXAMPLE 1

In our experiments we found that all essential oil do not produce synergistic effects with dermatophytes as in case of plant pathogens described in U.S. Pat. No. 6,231,685. Following tables presents the results of evaluation of antifungal activities of water or solvent extracts of garlic in combinations with the essential oils. As investigation contain solvent extract (propylene glycol) was found to more potent than the water extract and hence in subsequent experiments solvent extract was used for measuring the activities. The combinations of essential oils and garlic extracts were made according to their MICs (minimum inhibitory combinations). The table clearly reveal that the essential oil of *Eucalyptus* hybrid, *E. citriodora, Mentha citrata, M. arversis, Ocimum basilicum* (French basil), *Ocimum sanctum, Cymbopogon winteriamus, Trachyspermum ammi* (Thyme oil ), *Cumin cyminun, Anethum soya*, Cedar wood oil, sesame oil have produced the antagonostic effects in case of *Candida albicans* and *Trichophyton rubrum* when evaluated with garlic extract. But only selected oils viz. *Mentha spicata* van. Ganga, Cinnamon oil produced the synergistic effect when used together or separately with garlic extract. The activity increased to several folds when these combinations were added to constituent of essential oil like menthyl acetate. The additions of these isolates not only enhanced the activity but also mask the smell of garlic to generate a pleasant smell. The broth assay was carried out following the NCCLS documents published by National Committee for Clinical and Laboratory Standards (USA) and disc diffusion assay according to Bauer et al (Bauer et al, 1996, American Journal of Clinical Pathology, 45:493-496).

TABLE 1

Disc diffusion assay of garlic extract/essential oils alone and in combination.
(Net zone of inhibition in mm)

| Essential oils | *Trichophyton rubrum* Garlic extracts used alone 7 mm Essential oil used alone | *Trichophyton rubrum* Garlic extracts in combination with essential oil | *Candida albicans* (MTCC1637) Garlic extracts used alone 15 mm Essential oil used alone | *Candida albicans* (MTCC1637) Garlic extracts in combination with essential oil |
|---|---|---|---|---|
| *Eucalyptus globulus* | 3 | 10 | 5 | 20 |
| *Mentha citrata* | 3 | 5 | 8 | 21 |
| *Ocimum sanctum* | 15 | 10 | 17 | 25 |
| French basil oil | 6 | 7 | 11 | 17 |
| Thyme oil | 32 | 34 | 48 | 45 |
| Clocimum | 21 | 17 | 20 | 20 |
| Citronella oil | 15 | 17 | 14 | 20 |
| Fennel oil | 5 | 15 | 10 | 20 |
| Rosemary oil | 4 | 14 | 5 | 10 |
| Cumin oil | 15 | 17 | 25 | 25 |
| Cedar wood oil | — | 5 | — | 10 |
| Sesame oil | — | 6 | — | 5 |

TABLE 2

Broth assay of garlic extract in combination with essential oils
(using two fold dilution method) against *Candida albicans* MTCC1637)

| Essential oils | MIC of Essential oils | Concentration of garlic extract used in combination with oils | Reduction in the MIC of Essential oils | Fold enhancement on the basis of Reduction in the MIC of Essential oils | Type of Interaction | FIC Value |
|---|---|---|---|---|---|---|
| Garlic extract | 1/800 | | | | | |
| *Eucalyptus globulus* | 1/400 | 1/1600 | 1/800 | 2 | 1.0 | Indifference |
| | | 1/3200 | 1/800 | 2 | 0.75 | Additive |
| *Eucalyptus* hybrid | 1/1600 | 1/1600 | 1/1600 | 1 | 1.5 | Antagonistic |
| | | 1/3200 | 1/1600 | 1 | 0.75 | Additive |
| *Eucalyptus citridora* | 1/1600 | 1/1600 | 1/1600 | 1 | 1.5 | Antagonistic |
| | | 1/3200 | >1/1600 | — | >1.5 | Antagonistic |
| *Mentha citrata* | 1/800 | 1/1600 | >1/1600 | — | >1.5 | Antagonistic |
| | | 1/3200 | >1/1600 | — | >1.5 | Antagonistic |

TABLE 2-continued

Broth assay of garlic extract in combination with essential oils
(using two fold dilution method) against *Candida albicans* MTCC1637)

| Essential oils | MIC of Essential oils | Concentration of garlic extract used in combination with oils | Reduction in the MIC of Essential oils | Fold enhancement on the basis of Reduction in the MIC of Essential oils | Type of Interaction | FIC Value |
|---|---|---|---|---|---|---|
| *Mentha arvensis* | 1/1600 | 1/1600 | 1/1600 | 1 | 1.5 | Antagonistic |
|  |  | 1/3200 | >1/1600 | — | >1.5 | Antagonistic |
| Rosemary oil | 1/400 | 1/1600 | 1/1600 | 4 | 0.75 | Additive |
|  |  | 1/3200 | 1/800 | 2 | 0.75 | Additive |
| *Ocimum sanctum* oil | 1/800 | 1/1600 | 1/1600 | 2 | 1.0 | Indifference |
|  |  | 1/3200 | 1/1600 | 2 | 0.75 | Additive |
| French basil oil | 1/1600 | 1/1600 | >1/1600 | — | >1.0 | Antagonistic |
|  |  | 1/3200 | >1/1600 | — | >1.0 | Antagonistic |
| *Clocimum* | 1/1600 | 1/1600 | 1/3200 | 2 | 1.0 | Indifference |
| *Citronella* oil | 1/1600 | 1/1600 | 1/1600 | 1 | 1.5 | Antagonistic |
|  |  | 1/3200 | >1/1600 | — | >1.0 | Antagonistic |
| Thyme oil | 1/6400 | 1/1600 | 1/6400 | 1 | 1.5 | Antagonistic |
|  |  | 1/3200 | 1/6400 | 1 | 1.25 | Antagonistic |
| Cumin oil | 1/800 | 1/1600 | 1/800 | 1 | 1.5 | Antagonistic |
|  |  | 1/3200 | >1/800 | — | >1.5 | Antagonistic |
| Fennel oil | 1/400 | 1/1600 | >1/800 | — | >1.5 | Antagonistic |
|  |  | 1/3200 | >1/800 | — | >1.5 | Antagonistic |

TABLE 3

Broth assay of garlic extract in combination with one essential oils
(using two fold dilution method) against *Candida albicans*

| Essential oil/Plant compound/extract | MIC of essential oil/extract | Concentration of garlic extract used in combination with oil | Reduction in the MIC of oil | Fold enhancement on the basis of Reduction in the MIC of oil in combination | Type of Interaction | FIC value |
|---|---|---|---|---|---|---|
| Garlic extract | 1/800 |  |  |  |  |  |
| Menthyl acetate | 1/800 | 1/1600 | 1/1600 | 2 | Indifference | 1.0 |
|  |  | 1/3200 | 1/1600 | 2 | Additive | 0.75 |
|  |  | 1/6400 | 1/1600 | 2 | Additive | 0.625 |
| Cinnamon oil | 1/12800 | 1/1600 | 1/25600 | 2 | Indifference | 1.0 |
|  |  | 1/3200 | 1/12800 | 1 | Antagonistic | >1.0 |
|  |  | 1/6400 | 1/12800 | 1 | Antagonistic | >1.o |
| *Mentha spicata* | 1/800 | 1/1600 | 1/1600 | 2 | Indifference | 1.0 |
|  |  | 1/3200 | 1/1600 | 2 | Additive | 0.75 |
|  |  | 1/6400 | >1/800 | — | Antagonistic | >1.0 |

TABLE 4

Broth assay of garlic extract in combination with two essential oils/component
(using two fold dilution method) against *Candida albicans*

| Two oils used in combination and their Concentration used | Concentration of garlic extract used in combination with oils | Reduction in the MIC of 1st oil (used in series) | Fold enhancement on the basis of Reduction in the MIC of oil which is serially diluted (1) | Type of Interaction | FIC Value |
|---|---|---|---|---|---|
| Cinnamon (1/12800) + *Mentha spicata* (Ganga) (1/1600) | 1/1600 | 1/102400 | 8 | Additive | 0.625 |
| Cinnamon (1/12800) + *Mentha spicata* (Ganga) (1/3200) | 1/3200 | 1/25600 | 2 | Additive | 0.75 |
| Cinnamon (1/12800) + *Mentha spicata* (Ganga) (1/6400) | 1/1600 | 1/25600 | 2 | Indifference | 1.0 |
| Cinnamon (1/12800) + *Mentha spicata* (Ganga) (1/1600) | 1/6400 | 1/102400 | 8 | Synergistic | 0.25 |
| Cinnamon (1/12800) + *Mentha spicata* (Ganga) (1/3200) | 1/6400 | 1/25600 | 2 | Additive | 0.625 |
| *Mentha spicata* (Ganga) (1/1600) + Cinnamon (1/25600) | 1/3200 | 1/6400 | 8 | Synergistic | 0.25 |
| *Mentha spicata* (Ganga) (1/1600) + Cinnamon (1/25600) | 1/6400 | 1/3200 | 4 | Synergistic | 0.375 |

TABLE 4-continued

Broth assay of garlic extract in combination with two essential oils/component
(using two fold dilution method) against *Candida albicans*

| Two oils used in combination and their Concentration used | Concentration of garlic extract used in combination with oils | Reduction in the MIC of 1st oil (used in series) | Fold enhancement on the basis of Reduction in the MIC of oil which is serially diluted (1) | Type of Interaction | FIC Value |
|---|---|---|---|---|---|
| Menthyl acetate(1/1600) + Cinnamon (1/25600) | 1/3200 | 1/6400 | 8 | Synergistic | 0.375 |
| Menthyl acetate (1/1600) + Cinnamon (1/51200) | 1/3200 | 1/6400 | 8 | Synergistic | 0.375 |

Development and Testing of Formulation

In an effort to prepare a garlic based cream for topical application against superficial fungal infection of keratinised tissue of skin, selection of proper carrier solvent for garlic extraction was made as follows.

Preparation of Extract: 50 gm of raw garlic without removing the inner skin was properly homogenised in mortar & pestle along with 50 ml of
A. Distilled water
B. Vegetable oil (linseed oil)
C. Ethyl alcohol
D. Propylene glycol
E. Liquid paraffin After properly homogenisation the material was filtered after 1 hrs by double layer of muslin cloth and filtrate was used as garlic extract. The supernatant liquid was used as extract. The extracts in oil and liquid paraffin have two layers with emulsion at the junction of the water layer. The emulsion was rejected and the volume of the remaining supernatant was made up of to 50 ml by adding appropriate amount of respective solvent. The solution was utilized for testing of antifungal activity as mother solution. The antifungal activity was tested [Bauer et al, 1996, Journal of Clinical Pathology, 45:493-496], which revealed that the garlic extracted in propylene glycol, is the best solvent for antifungal activity.

It was further observed that the activity is lost by keeping the homogenised material more than 24 hrs at room temperature (30-35°). The propylene glycol extract when tested after 15 days of storage at room temperature no activity was recorded. Similarly deterioration of activity was recorded for the extract when stored at 5° C. for 15 days. The pH of garlic with water was recorded to be 5.8 while the propylene glycol extract (50 g garlic+50 g propylene glycol) was 6.17. The activity of garlic extract in propylene glycol was slightly increased in acidic pH 4.5 by adding citric acid. When the propylene glycol extract was warmed up to 40° to 60° for 30 minute in water bath the activity decreased.

TABLE 5

| | *Candida albican* (MTCC1637) | *Trichophyton rubrum* |
|---|---|---|
| 1. Garlic juice | — | — |
| 2. Garlic extract in propylene glycol | 15 | 7 |
| 3. Garlic juice + citric acid pH 4.5 | 3 | 3 |
| 4. Garlic juice propylene glycol at 40° | 2 | 2 |
| 5. Garlic juice propylene glycol at 60° | 1 | 2 |

The combination of cinnamon oil with menthyl acetate (isolated from the essential oil of *M. arvensis*) and cinnamon oil with the essential oil of *M. spicata* variety Ganga were found to be having synergistic effect on antifungal activity when used along with garlic extract (propylene glycol). In all the cases the MIC of both garlic extract and essential oils have been drastically reduced enhancing the activity of garlic and also masking the smell. On the basis of above results the following combinations were prepared.

Preparations

| Ingredients | Stearyl alcohol - | 4 gm |
|---|---|---|
| | Cetyl alcohol | 2 gm |
| | White petrolatum - | 4 gm |

Oil, constituent and extract of garlic as per quantity provided below.

Propylene glycol remaining amount upto 20 g total weight.

| Product | Concentration of garlic extract in 20 g cream | Concentration of oils and/or constituent ml per 20 gm total weight | |
|---|---|---|---|
| Cream No 1 | 0.25 g | *M. spicata* Var Ganga | 0.4 |
| Cream No 2 | 0.5 g | Menthyl acetate | 0.04 |
| Cream No 3 | 0.5 g | *M. spicata* Var Ganga | 0.04 |
| Cream No 4 | No extract | Menthyl acetate Cinnamon | .02 .002 |
| Cream No 5 | 0.5 g | Menthyl acetate Cinnamon | 0.02 0.002 |
| Cream No 7 | 0.6 g | Geraniol | 0.2 |
| Cream No 8 | No extract | Geraniol | 0.2 |

Method for Preparing Cream

Specified quantities of stearyl alcohol and cetyl alcohol was melted along with white petrolatum and propylene glycol in a water bath (70-75° C.)with constant stirring. The mixture was cooled down to 35-40° C. and required amount of extract followed by essential oil were added with thorough mixing for homogenisation. The cream was left for curing with occasional mixing at periodic intervals 3 to 4 times. The cream thus prepared were transferred to plastic covered containers till the antifungal evaluation were made.

EXAMPLE 2

TABLE 6

Antifungal evaluation by hole diffusion method

| Product | Candida albicans | Trichophyton rubrum | Microsporum gypseum | Epidermophyton floccosum |
|---|---|---|---|---|
| 1 | 4 | 14 | 69 | 38 |
| 2 | — | 2 | 10 | 8 |
| 3 | — | 2 | 22 | 18 |
| 4 | — | — | — | — |
| 5 | — | — | 12 | 14 |
| 6 | — | — | 10 | 13 |
| 7 | — | — | 10 | 18 |

The combinations utilised in cream No 1 is promising as per the result and this combination was taken for further improvement.

EXAMPLE 3

Two creams were prepared for further improvement in cream 1

1A. The concentrations of oil and garlic extract were doubled.
1B. The concentration of oil was doubled To maintain the cream to 20 gm the concentration of propylene glycol was changed accordingly.

Method of preparation—Ingredients for 20 gm. Cream

Stearyl alcohol 4 g
Cetyl alcohol 2 g
Petrolatum white 4 g
Propylene glycol remaining amount to make the cream to 20 g

| Product | Conc. of garlic extract (g/20 g). | Essential oil of M. spicata Var Ganga (ml in 20 g) |
|---|---|---|
| Cream 1 (A) | 0.5 gm extract | 0.8 ml oil |
| Cream 1 (B) | 0.25 gm extract | 0.8 ml oil |

Antifungal activity of cream 1 (A) ad 1 (B) & comparison with mixture of extract and oil (Net zone of inhibition in mm)

| Product | Candida albicans | Trichophyton rubrum | Microsporum gypseum | Epidermophyton floccosum |
|---|---|---|---|---|
| Cream 1 (A) | 10 | 34 | CL | 53 |
| Cream 1 (B) | 7 | 35 | CL | 58 |
| Mentha spicata var. Ganga Oil + garlic extract | 13 | 34 | CL | CL |

CL. Complete Lysis After 5-7 Days

For further improvement more combination of garlic extract and *M. spicata* var. Ganga was tried.

EXAMPLE 4

All Ingredients and the procedure adapted were same as described in example 3 and only the concentration of active ingredients were changed as follows.

| Product | Garlic extract (g/20 g). | Oil M. spicata var Ganga ml/20 g |
|---|---|---|
| Cream 8 (1) | 0.6 | 1.0 |
| Cream 8 (2) | 0.3 | 0.5 |

Anti fungal evaluations by hole diffusion method (Net zone of inhibition in mm)

| Product | Candida albicans | Trichophyton rubrum | Microsporum gypseum | Epidermophyton floccosum |
|---|---|---|---|---|
| Cream 8 (1) | 14 | 50 | 70 | 65 |
| Cream 8 (2) | 5 | 15 | 55 | 55 |

The combination Cream 9 (1) was observed to be the best as compared to all the combination prepared.

EXAMPLE 5

In this experiment the concentration of active ingredients were not changed. The modification was done in the base. The quantity of cetyl alcohol was reduced.

Preparation of Cream

| Ingredients | |
|---|---|
| Stearyl alcohol | 2.0 g. |
| Cetyl alcohol | 1.0 g. |
| White petrolatum | 2.0 g |
| Propylene glycol | 4.2 g. |
| Garlic extract. | 0.3 g |
| M. spicata (Ganga) oil | 0.5 ml |
| | 10 gm. |

Stability of the anti dermatophytic activities of the formulation by hole diffusion method (Net zone of inhibition in mm)

| Cream 9 | Candida albicans | Trichophyton rubrum | Microsporum gypseum* | Epidermophyton floccosum* |
|---|---|---|---|---|
| Freshly prepared cream | 18 | 28 | 60* | 55* |
| After 3 months | 22 | 25 | 66* | 50* |
| After 6 months | 12 | 19 | 45* | 46* |
| After 12 months | 13 | 21 | 45 | 45* |

*Complete lysis occurs after 5–7 days of incubation.

From the experiments of other non published work it was found that if the quantity of white petrolatum is replaced by propylene glycol the efficacy of the cream is further improved. So the final cream was prepared by adding the appropriate amount of propylene glycol and instead of using filtrate the extract was centrifuged at 10000 rpm for 10 min at room temperature. The supernatant was used in the preparation of the cream. This modification provided a better texture and smoothness of the cream and also was easily spreadable on the skin surface.

| Cream 10 | Candida albicans | Trichophyton rubrum | Microsporum gypseum* | Epidermophyton floccosum* |
|---|---|---|---|---|
| Freshly prepared cream | 21 | 33 | 73 | 44 |
| After 3 months | 20 | 30 | 73 | 67 |
| After 4 months | 21 | 33 | CL | CL |

CL. Complete Lysis After 5-7 Days of Incubation.

EXAMPLE 6

Comparative evaluation of present formulation with the creams available in market. (Net zone of inhibition in mm)

| Formulation | Candida albicans | Trichophyton rubrum | Microsporum gypseum | Epidermophyton floccosum |
|---|---|---|---|---|
| Candid | 20 | 16 | 40 | 20 |
| Ring guard | 17 | — | 33 | 30 |
| Quadiderm | 15 | 17 | 27 | 20 |
| Krack | — | — | 18 | 15 |
| Lichensa | 2 | — | 20 | 19 |
| Cream 10 | 22 | 25 | 60 | 50 |

The cream was subjected to clinical trials on 10 volunteers suffering from superficial fungal infection and all volunteers reported reduction in the infection in three days of application two times a days. After one week of application 8 volunteers reported complete cure.

The cream samples were evaluated for primary skin irritation test in rabbits as per standard protocol of OECD guidelines and in all samples the primary irritation index was calculated to be 0.

EXAMPLE 7

Garlic as the Enhancer of Activity of Essential Oil

The minimum inhibitory concentrations of the essential oils were decreased to several folds in presence of the garlic extract (Propylene glycol) indicating the enhancing and synergistic activity of garlic extract on activity of essential oils.

| MIC of Essential oils | Garlic extract | MIC of Essential oils in Combination with garlic extract |
|---|---|---|
| 1/3200 Clove oil | 1/800 | 1/12800 |
| 1/1600 Coriander oil | 1/800 | 1/12800 |
| 1/1600 Mentha piperita | 1/800 | 1/25600 |
| 1/1600 Eukalyptus globulus | 1/800 | 1/6400 |
| 1/1600 Ocimum santum | 1/800 | 1/6400 |

EXAMPLE 8

Mechanism of Action

The improved preparation (Cream 10) was also tested against isolated resistant mutants of *Candida albicans* against Clotrimazole, Amphotericin B and Nystatin. As most of the available antifungal available in the market contain these compounds the cream of invention/improved formulation was compared with them. Clotrimazole inhibits the biosynthesis of ergosterol in *Candida albicans*. The resistant mutants produce modified enzyme which can not bind to the azole group of compounds. But the compounds which inhibits more to the resistant mutants may be taken as potent inhibitor of ergosterol biosynthesis, which was observed in the improved preparation. Similarly, Amphotericin B and Nystatin resistant mutants were developed in the laboratory and the activity of the improved preparation was tested against a series of mutants showing different degree of resistance. The mutants resistant against Amphotericin B are also resistant against Nystatin. The polyenes binds to ergosterol and make it non-available for cell membrane biosynthesis there by inhibiting the growth. In mutants the sterol can not binds to the polyenes and hence resistance develops. The improved preparation also showed considerable activity against these mutants indicating the reduced availability of ergosterol for membrane. Hence the preparation (Cream 10) inhibit the biosynthesis of ergosterol and also makes it unavailable for membrane biosynthesis. The result of the experiments conducted as "hole diffusion assay" are provided below. All the activities of the preparation are better than the tested market available preparations and inhibit the growth of the fungus by inhibiting ergosterol biosynthesis and also making the sterol non-available for cell membrane biosynthesis.

Evaluation of improved preparation by hole diffusion method against *Candida albicans* WT and Azole(clotrimazole) resistant mutants(Net zone of inhibition in mm)

| Preparations | Candida albicans WT | Candida albicans mutants | | | |
|---|---|---|---|---|---|
| | | Clo 31 | Clo 128 | Clo 39 | Clo 29 |
| Lichensa | 2 mm | — | — | — | — |
| Candid | 20 mm | 8 | 3 | 3 | 5 |
| Ringguard | 17 mm | 10 | 10 | 8 | 10 |
| Krack | — | — | — | — | — |
| Cream 10 | 21 mm | 33 | 23 | 28 | 40 |

Evaluation of improved preparation by hole diffusion method against *Candida albicans* (MTCC 1637) and AmphotericinB resistant mutants (Net zone of inhibition in mm).

| Preparations | Candida albicans WT | Candida albicans mutants | | | |
|---|---|---|---|---|---|
| | | A1 | A10 | A15 | A17 |
| Lichensa | 2 mm | — | 3 | — | — |
| Candid | 20 mm | 8 | 9 | 9 | 5 |
| Ringguard | 17 mm | 4 | 8 | 5 | 5 |
| Krack | — | — | — | — | — |
| Cream 10 | 21 mm | 10 | 16 | 13 | 9 |

Evaluation of improved preparation by hole diffusion method against *Candida albicans* (MTCC 1637) and Nystatin resistant mutants (Net zone of inhibition in mm)

| Preparations | Candida albicans Wild type | Candida albicans mutants | | | |
|---|---|---|---|---|---|
| | | N7 | N8 | N16 | N30 |
| Lichensa | 2 mm | 8 | 7* | — | 14* |
| Candid | 20 mm | 14 | 10 | 11* | 11 |
| Ringguard | 17 mm | 17 | 11 | 3 | 7 |
| Krack | — | — | — | — | — |
| Cream 10 | 21 mm | 20 | 20 | 14 | 20 |

*fungistatic zone

EXAMPLE 7

Garlic as the Enhancer of Activity of Essential Oil

The minimum inhibitory concentrations of the essential oils were decreased to several folds in presence of the garlic extract (Propylene glycol) indicating the enhancing and synergistic activity of garlic extract on activity of essential oils.

| MIC of Essential oils | Garlic extract | MIC of Essential oils in Combination with garlic extract |
|---|---|---|
| 1/3200 Clove oil | 1/800 | 1/12800 |
| 1/1600 Coriander oil | 1/800 | 1/12800 |
| 1/1600 *Mentha piperita* | 1/800 | 1/25600 |
| 1/1600 *Eukalyptus globulus* | 1/800 | 1/6400 |
| 1/1600 *Ocimum santum* | 1/800 | 1/6400 |

EXAMPLE 8

Mechanism of Action

The improved preparation (Cream 10) was also tested against isolated resistant mutants of *Candida albicans* against Clotrimazole, Amphotericin B and Nystatin. As most of the available antifungal available in the market contain these compounds the cream of invention/improved formulation was compared with them. Clotrimazole inhibits the biosynthesis of ergosterol in *Candida albicans*. The resistant mutants produce modified enzyme which can not bind to the azole group of compounds. But the compounds which inhibits more to the resistant mutants may be taken as potent inhibitor of ergosterol biosynthesis, which was observed in the improved preparation. Similarly, Amphotericin B and Nystatin resistant mutants were developed in the laboratory and the activity of the improved preparation was tested against a series of mutants showing different degree of resistance. The mutants resistant against Amphotericin B are also resistant against Nystatin. The polyenes binds to ergosterol and make it non-available for cell membrane biosynthesis there by inhibiting the growth. In mutants the sterol can not binds to the polyenes and hence resistance develops. The improved preparation also showed considerable activity against these mutants indicating the reduced availability of ergosterol for membrane. Hence the preparation (Cream 10) inhibit the biosynthesis of ergosterol and also makes it unavailable for membrane biosynthesis. The result of the experiments conducted as "hole diffusion assay" are provided below. All the activities of the preparation are better than the tested market available preparations and inhibit the growth of the fungus by inhibiting ergosterol biosynthesis and also making the sterol non-available for cell membrane biosynthesis.

Evaluation of improved preparation by hole diffusion method against *Candida albicans* WT and Azole(clotrimazole) resistant mutants(Net zone of inhibition in mm)

| Preparations | Candida albicans WT | Candida albicans mutants | | | |
|---|---|---|---|---|---|
| | | Clo 31 | Clo 128 | Clo 39 | Clo 29 |
| Lichensa | 2 mm | — | — | — | — |
| Candid | 20 mm | 8 | 3 | 3 | 5 |
| Ringguard | 17 mm | 10 | 10 | 8 | 10 |
| Krack | — | — | — | — | — |
| Cream 10 | 21 mm | 33 | 23 | 28 | 40 |

Evaluation of improved preparation by hole diffusion method against *Candida albicans* (MTCC 1637) and AmphotericinB resistant mutants (Net zone of inhibition in mm).

| Preparations | Candida albicans WT | Candida albicans mutants | | | |
|---|---|---|---|---|---|
| | | A1 | A10 | A15 | A17 |
| Lichensa | 2 mm | — | 3 | — | — |
| Candid | 20 mm | 8 | 9 | 9 | 5 |
| Ringguard | 17 mm | 4 | 8 | 5 | 5 |
| Krack | — | — | — | — | — |
| Cream 10 | 21 mm | 10 | 16 | 13 | 9 |

Evaluation of improved preparation by hole diffusion method against *Candida albicans* (MTCC 1637) and Nystatin resistant mutants (Net zone of inhibition in mm)

| Preparations | Candida albicans Wild type | Candida albicans mutants | | | |
|---|---|---|---|---|---|
| | | N7 | N8 | N16 | N30 |
| Lichensa | 2 mm | 8 | 7* | — | 14* |
| Candid | 20 mm | 14 | 10 | 11* | 11 |
| Ringguard | 17 mm | 17 | 11 | 3 | 7 |
| Krack | — | — | — | — | — |
| Cream 10 | 21 mm | 20 | 20 | 14 | 20 |

*fungistatic zone

The invention provides a novel formulation based on the synergistic action of garlic extract and essential oil of *M. spicata* var Ganga or cinnamon oil alone or in combination with both which may further be enhanced by menthyl acetate or Geraniol. Further the invention provides a method of preparation of the synergistic combination. The shelf life of the said invention was observed to be more than one year. The oil of *M. spicata* var Ganga act as preservative for the cream. The cream is a potent anti-dermatophytic as described and illustrated and evaluated in human volunteers.

We claim:

1. An antifungal formulation comprising a garlic extract in propylene glycol, essential oil of *M. spicata* var. Ganga, and cinnamon oil, said garlic extract and essential oil of *M. spicata* and cinnamon oil being present in the formulation in respective amounts effective to provide the formulation with synergistic anti-dermatophytic activity.

2. A formulation as claimed in claim 1 further comprising a base, wherein the base is prepared by mixing stearyl alcohol, cetyl alcohol and propylene glycol at 70-75° C. over a water bath and cooling down the preparation with constant stirring up to ambient temperature and then curing for 48 hours in a covered beaker with occasional mixing.

3. A formulation as claimed in claim 1 wherein the garlic extract is present in an amount of 1-3%, and wherein the formulation comprises a base and menthyl acetate or geraniol that is added to the base at a temperature of 30-35° C.

4. A formulation as claimed in claim 1 wherein the garlic extract in propylene glycol is present in a concentration in the range of 1%-2.5%.

5. A formulation as claimed in claim 1 wherein the essential oil of *M. apicata* var Ganga is present in a concentration in the range of 2%-5%.

6. A formulation as claimed in claim 1 wherein the cinnamon oil is present in a concentration in the range of 0.01%.-0.8%.

7. A formulation as claimed in claim 1 wherein the respective amounts of the garlic extract and oil provide the formulation with synergistic anti-dermatophytic activity against dermatophytic fungi selected from the group consisting of *Candida, Trichophyton, Microsporum* and *Epidermophyton*.

8. A formulation as claimed in claim 1 wherein the shelf life of the formulation is more than one year.

9. A formulation as claimed in claim 1 wherein the antifungal formulation is active against dermatophytic fungi which are sensitive to synthetic antifungal compounds selected from the group consisting of azoles and polyenes.

10. A formulation as claimed in claim 1 wherein the antifungal formulation is active against dermatophytic fungi and the antifungal formulation shows clearing of the fungal culture indicating clear lysis.

11. A formulation as claimed in claim 1, further comprising menthyl acetate or geraniol in an amount effective to enhance the anti-dermatophytic activity.

12. A formulation as claimed in claim 11 wherein the menthyl acetate is present in a concentration in the range of 0.3%-1.2%.

13. A formulation as claimed in claim 11 wherein the geraniol is present in a concentration of about 1%.

14. A method for the treatment of dermatophytic fungi comprising (a) providing the formulation of claim 1, and (b) administering to a subject infected with a dermatophytic fungus an effective amount of the formulation.

15. A method as claimed in claim 14 wherein the formulation comprises a base prepared by mixing stearyl alcohol, cetyl alcohol and propylene glycol at 70-75° C. over a water bath and cooling with constant stirring up to ambient temperature and then curing for 48 hours in a covered beaker with occasional mixing.

16. A method as claimed in claim 14 wherein the garlic extract is present in an amount of 1-3% and wherein the formulation comprises a base and menthyl acetate or geraniol is added to the base at a temperature of 30-35° C.

17. A method as claimed in claim 14 wherein the garlic extract in propylene glycol is present in a concentration in the range of 1%-2.5%.

18. A method as claimed in claim 14 wherein the essential oil of *M spicata* var. Ganga is present in a concentration in the range of 2%-5%.

19. A method as claimed in claim 14 wherein the cinnamon oil is present in a concentration in the range of 0.01%-0.8%.

20. A method as claimed in claim 14 wherein the dermatophytic fungus is selected from the group consisting of *Candida, Trichophyton, Microsporum* and *Epidermophyton*.

21. A method as claimed in claim 14 wherein the formulation is active against dermatophytic fungi by making a sterol non-available for cell membrane biosynthesis.

22. A method as claimed in claim 14 wherein the antifungal formulation is active against dermatophytic fungi which are sensitive to synthetic antifungal compounds selected from the group consisting of azoles and polyenes.

23. A method as claimed in claim 14 wherein the antifungal formulation is active against dermatophytic fungi and the antifungal formulation shows clearing of a fungal culture indicating clear lysis.

24. A method as claimed in claim 14, wherein the formulation further comprises menthyl acetate or geraniol in an amount effective to enhance the anti-dermatophytic activity.

25. A method as claimed in claim 24, wherein the menthyl acetate is present in a concentration in the range of 0.3%-1.2%.

26. A method as claimed in claim 24, wherein the geraniol is present in a concentration of about 1%.

* * * * *